United States Patent [19]

Holter

[11] 4,086,281

[45] Apr. 25, 1978

[54] PROCESS FOR PRODUCING MONO-SUBSTITUTED ALKYLRESORCINOL ISOMERS

[75] Inventor: Samuel N. Holter, Pittsburgh, Pa.

[73] Assignee: Koppers Company, Inc., Pittsburgh, Pa.

[21] Appl. No.: 732,477

[22] Filed: Oct. 14, 1976

Related U.S. Application Data

[63] Continuation-in-part of Ser. No. 564,785, Apr. 3, 1975, abandoned.

[51] Int. Cl.² .............................................. C07C 39/08
[52] U.S. Cl. ................................. 260/621 R; 260/625
[58] Field of Search ........... 260/621 R, 621 E, 624 E, 260/625, 624 C

[56] References Cited

U.S. PATENT DOCUMENTS 3,426,358  2/1969  Schlitching et al. ................. 260/625
3,642,912  2/1972  Sharp ................................. 260/621 R
3,992,455  11/1976 Leston ............................... 260/621 R Primary Examiner—James O. Thomas, Jr.
Assistant Examiner—Werren B. Lone
Attorney, Agent, or Firm—Kenneth J. Stachel; Oscar B. Brumback

[57] ABSTRACT

Mono-substituted alkylresorcinol isomers, predominantly the 5-alkylresorcinol isomer, are produced by reacting resorcinol and an aliphatic alcohol having 1-3 carbon atoms in the vapor phase in the presence of an acidic catalyst and by separating the resulting mono-substituted alkylresorcinol isomers from other alkylated hydroxyaromatic compounds and unreacted resorcinol. The molar ratio of alcohol to resorcinol is in the range of greater than 1:1 to 3:1. The reaction time in a batch operation and the liquid hourly space velocity in a continuous operation are controlled so not to allow the mono-substituted alkylresorcinol to undergo further alkylation.

10 Claims, No Drawings

PROCESS FOR PRODUCING MONO-SUBSTITUTED ALKYLRESORCINOL ISOMERS

CROSS-REFERENCE TO RELATED APPLICATIONS

This application is a continuation-in-part of application Ser. No. 564,785 filed Apr. 3, 1975, now abandoned.

BACKGROUND OF THE INVENTION

This invention relates to the alkylation of resorcinol to produce mono-substituted alkylresorcinol isomers. More particularly, this invention relates to the alkylation of resorcinol to produce predominantly 5-alkylresorcinol along with 2-alkylresorcinol.

Phenolic compounds and especially phenol have been alkylated by many methods in the art. Phenols have been alkylated both randomly and selectively by reaction with an olefin, alcohol or ether in the presence of a particular catalyst. One method of preparing ortho substituted alkylphenols is by the vapor phase reaction of at least one alcohol with at least one phenol in the presence of at least one titanium dioxide catalyst. One method for randomly alkylating a phenolic compound is by reacting the phenolic compound with an alcohol or an ether in the vapor phase in the presence of a metal oxide condensation catalyst at a superatmospheric pressure. In this latter method, the phenolic compound is usually a phenol but it may also be a polyhydric phenol like resorcinol. When resorcinol is used, it is converted into monoethyl-, diethyl-, triethyl-, or tetraethyl resorcinol. Neither of these methods are used to alkylate resorcinol partially, i.e., to limit alkylation to one alkyl group per aromatic ring, while alkylating resorcinol selectively, i.e., alkylation in a particular position on the aromtic ring.

Resorcinol is a polyhydric phenol with a hydroxyl group at the 1 and 3 positions on the aromatic ring. Chemical reactions of resorcinol involve both the two hydroxyl groups and the activated nuclear hydrogens in a manner which resembles phenol but is in many respects peculiar to resorcinol. Resorcinol is highly reactive because of the reinforcing action of the two hydroxyl groups. Resorcinol is substituted initially at the position on the aromatic ring where the two hydroxyl groups reinforce thus yielding a resorcinol substituted in the fourth position on the aromatic ring. Any selective partial alkylation of resorcinol at a position other than the fourth position presents inevitable difficulties.

The synthetic routes to an alkylresorcinol that is partially alkylated at a position other than the 4th position on the aromatic ring are multistep and give low overall yields. For example, a 50% yield of a 2-methyl-resorcinol is obtained by hydrogenation of resorcinol and methylation of the resulting dihydroresorcinol to 2-methylcyclohexane-1,3-dione which on treatment with bromine is converted into 4,6-dibromo-2-methylresorcinol and finally hydrogenolysis of the dibromo derivative to produce the 2-methylresorcinol. Another example is that 5-methylresorcinol can be prepared by a five-step synthesis starting with p-toluidine or a four-step synthesis starting from ethyl crotonate. The five-step synthesis involves acetylation, two-step nitration, reductive hydrogenation, and hydrolysis.

Illustrative of the prior art pertinent to alkylation of phenolic compounds with alcohols are U.S. Pat. Nos. 2,448,942 (Winkler et al.); 3,642,912 (Sharp et. al.); 2,678,951 (Smith et al.); 3,422,156 (Thoma); and 3,426,358 (Schlechting et al.). The process of the present invention is deemed patentable over this prior art because this art fails to teach or disclose a process for producing mono-substituted alkylresorcinol isomers, predominantly the 5-alkylresorcinol isomer along with smaller amounts of 2-alkylresorcinol isomer and 4-alkylresorcinol isomer.

The alkylresorcinol isomers produced by the alkylation of resorcinol with an aliphatic alcohol are useful as chemical intermediates, corrosion inhibitors, photographic chemicals and as components of epoxy resins and polymers.

It is the primary object of this invention to provide a process to produce the three alkylresorcinol isomers, 2-, 4-, and 5-alkylresorcinol, simultaneously in one step.

It is a further object of this invention to provide a process to produce the three alkylresorcinol isomers in such a manner that the major alkylresorcinol isomer produced is the 5-alkylresorcinol along with 2-alkylresorcinol and both can be separated in good yields.

SUMMARY OF THE INVENTION

In accordance with the present invention a process is provided for producing simultaneously mono-substituted alkylresorcinol isomers, predominantly 5-alkylresorcinol along with lesser amounts of 2-alkylresorcinol. The process of the present invention comprises the reaction in the vapor phase of resorcinol with a molar excess of an aliphatic alcohol having one to three carbon atoms to produce the isomers of mono-substituted alkylresorcinol, predominantly 5-alkylresorcinol along with lesser amounts of other alkylated hydroxyaromatic compounds and unreacted resorcinol and separation of the isomers of the mono-substituted alkylresorcinols from the other compounds present.

The reaction of resorcinol and a $C_1$–$C_3$ aliphatic alcohol is conducted at a molar ratio of alcohol to resorcinol of greater than 1:1 to 3:1 in the presence of an acidic catalyst. Also, the reaction is conducted in the vapor phase at a temperature at or above the boiling point of resorcinol which is 275.9° C. at atmospheric pressure. The pressure used for the reaction is atmospheric pressure but elevated pressures may also be used. The reaction time in a batch operation cannot be too long and the liquid hourly space velocity (LHSV) in a continuous operation cannot be too low and should be less than about 0.2 volume of reactants per gross volume of catalyst per hour. If either of these circumstances occurs, i.e., a long reaction time or a low LHSV, the amount of higher alkylated resorcinols produced will be increased. This occurs because the mono-substituted alkylresorcinol will undergo further alkylation to the higher alkylated resorcinol.

The aliphatic alcohol has one to three carbon atoms because the higher the number of carbons in the alcohol, the more difficult it is to conduct the alkylation reaction. An alcohol with the higher number of carbons, i.e., three or more, has a tendency to dealkylate as well as alkylate. The larger carbon groups are removed more easily from the aromatic ring. A three carbon alkyl group is removed from the aromatic ring around 300° C. whereas the single carbon group, methyl, is removed from the aromatic ring at a temperature around 600° C. When an alcohol with two or three carbon atoms is used in the reaction, the pressure must be increased to favor the alkylation reaction over the dealkylation reaction. The aliphatic alcohols with one to three carbon atoms which can be used in the process of this invention include saturated alcohols like methanol, ethanol, propanol and isopropanol and unsaturated alcohols like allyl alcohol, propargyl alcohol and halogenated or nitrated derivatives thereof. Preferably the saturated alcohols: methanol, ethanol, propanol and isopropanol are used.

The acidic catalyst used may generally be described as any Lewis acid or Bronsted acid. Some examples are: acid activated clays, like attapulgus clay; activated bauxite, like porocel, a product manufactured by Englehard Industries; titanium dioxide; alumina; silica alumina; and Friedel Crafts catalysts. When alumina catalysts are used, the hard alumina catalysts, such as those manufactured by Houdry Process and Chemical Company, are preferred. The above catalysts may be employed either alone or mixed with one another.

Under the above conditions of reaction, a mixture is produced that contains mostly mono-substituted alkylresorcinol isomers along with a lesser amount of other alkylated hydroxyaromatic compounds and unreacted resorcinol. The separation of the mono-substituted alkyresorcinol isomers from the other alkylated hydroxyaromatic compounds and unreacted resorcinol in this mixture may be by fractional distillation, extraction, crystallization or any other method known to those skilled in the art. The separation of the 2 isomer or 2-alkylresorcinol from the 5 isomer or 5-alkylresorcinol may also be by fractional distillation, extraction or crystallization. The extraction may be selective extraction in ethylene chloride and the crystallization may be fractional crystallization of a 275°–290° C. boiling fraction dissolved in ethylene chloride. Other separation methods known to those skilled in the art include the Bergues process for separating alkylated resorcinols and for separating 5-alkylresorcinol and fractional distillation after treating the mixture of alkylresorcinols with hexamethyldisilazane.

Also, 5-alkylresorcinol may be separated from the product mixture while leaving 2- and 4-alkylresorcinol isomers in the mixture. Then, this mixture is recycled to the reaction of resorcinol with the aliphatic alcohol. During this reaction, the added recycled alkylresorcinols will isomerize to some degree to 5-alkylresorcinol.

The term "alkyl" refers to a aliphatic hydrocarbon group having one to three carbon atoms.

The term "mono-substituted alkylresorcinol isomers" refers to those compounds having only one alkyl group on the aromatic ring of resorcinol. These compounds include 2-, 4-, and 5-alkylresorcinol.

The term "other alkylated hydroxyaromatic compounds" include: m-alkyloxyphenol and higher alkylated resorcinols such as di-, tri-, and tetraalkylresorcinol.

DETAILED DESCRIPTION OF THE INVENTION

The process of this invention may be conducted in a batch operation in a typical alkylation autoclave but a continuous operation is preferred. When a batch operation is used, the reaction time is determined by periodic sampling. When the quantity of 5-alkylresorcinol reaches a maximum and begins to decrease, then the reaction should be stopped. The preferred alcohol used to react with resorcinol is methanol so that mono-substituted methylresorcinols and preferably 5-methylresorcinol and 2-methylresorcinol are produced. The reaction of methanol with resorcinol is conducted in the vapor phase.

In the continuous operation of the process of this invention, the resorcinol and methanol may be added either separately or together to a reaction vessel containing an acidic catalyst. It is preferred to add the resorcinol and methanol together. These reactants are added to the vessel in a molar ratio of methanol to resorcinol in the range of greater than 1:1 to 3:1 and preferably 2:1. The reaction vessel is any alkylation vessel known to those skilled in the art that is capable of sustaining elevated temperatures. This vessel may be constructed of steel.

The acidic catalyst used is preferably an alumina catalyst. An example of a good alumina catalyst is Houdry 100S manufactured by Houdry Process and Chemical Company. This catalyst is composed of 98.5 wt. % $Al_2O_3$ and 0.1–0.2 wt. % $Na_2O$. Its physical properties are: surface area 75–85 (m²/g), bulk density 0.78–0.82 kg/1, pellet density 1.28–1.34 kg/1, true density 3.6–3.7 kg/1, porosity 60–65 vol. %, crushing strength 15–30 lbs. and knife-edge hardness 5–10 1000 gm.

The resorcinol and methanol are added to the reaction vessel at a liquid hourly space velocity (LHSV) in the range of volume of reactants per gross volume of catalyst of about 0.2 to around 0.55 and in the preferred range of 0.3–0.45. The LHSV cannot be too low because the mono-methylated resorcinols would be subject to further methylation to the higher methylated resorcinols. The reactants and catalyst in the vessel are at a temperature generally in the range of about 350° to around 415° C. and preferably 350° C. to around 385° C. This temperature is the maximum temperature in the catalyst bed within the reaction vessel rather than an average temperature. The pressure of the vessel is preferably atmospheric pressure. Under these conditions, resorcinol and methanol react to form a mixture of methylated products of resorcinol. The percent conversion of resorcinol at these conditions is less than 100%. When the reaction approaches 100% conversion, the possibility of obtaining a less selective product mixture increases. Conversion of resorcinol at 100% may be used if the LHSV is low enough.

After a period of use in catalyzing the reaction, the Houdry 100S catalyst may develop a carbon coating that would deactivate it. This deactivated catalyst may be regenerated by any method known to those skilled in the art. Such a method may be the oxidizing of the carbon by passing hot air over the catalyst.

The product produced from the reaction of resorcinol and methanol at the above conditions is a mixture containing mainly the mono-substituted methylresorcinol isomers, predominantly 5-methylresorcinol and a lesser amount of 2-methylresorcinol and preferably a smaller amount of 4-methylresorcinol. The mixture also contains minor amounts of other methylated hydroxyaromatics and some unreacted resorcinol. The other methylated hydroxyaromatics include: m-methoxy phenol and the higher methylated resorcinols, di-, tri-, and tetramethylresorcinols.

This product mixture is introduced into a separation vessel or series of separation vessels. This vessel or these vessels may be fractional distillation vessels. In these vessels, the mono-substituted methylresorcinol isomers are separated from unreacted resorcinol and other methylated hydroxyaromatic compounds. The boiling points of these compounds are substantially close to each other so that a good separation in a single 0.55, and the product produced contained a very small amount of the desired 5-methylresorcinol.

Table I

Partial Methylation of Resorcinol in the Vapor Phase

| Run | Catalyst | LHSV | Temp. °C. | Total Time(hr) | % Conversion Resorcinol | Products | | | | | | |
|---|---|---|---|---|---|---|---|---|---|---|---|---|
| | | | | | | m-methoxy phenol | Unknowns | Resorcinol | 2- | 4- | 5- | Higher |
| 1 | Houdry 100S 1:1:1 MeOH[a]/ Resorcinol/ H$_2$O | 0.30 | 359 | 2.0 | 71.9 | 4.5 | 1.0 | 27.9 | 18.0 | 19.4 | 19.8 | 9.4 |
| 2 | Houdry 100S 2:1 MeOH/ Resorcinol | 0.36 | 385 | 3.5 | 70.9 | 5.7 | 7.4 | 28.9 | 0.6 | 17.6 | 36.5 | 3.3 |
| 3 | " | 0.24 | 381 | 19.25 | 81.5 | 6.7 | 0.5 | 18.4 | 32.4 | 11.9 | 28.4 | 1.7 |
| 4 | " | 0.40 | 376 | 3.0 | 92.1 | 3.7 | 5.7 | 7.8 | 17.1 | 11.4 | 21.3 | 33.0 |
| 5 | " | 0.33 | 374 | 8.25 | 97.8 | 7.3 | 3.6 | 2.2 | 32.2 | 0.4 | 48.8 | 5.5 |
| 6 | " | 0.31 | 365 | 8.0 | 90.8 | 8.1 | 0.9 | 9.1 | 30.3 | 0.6 | 47.0 | 4.0 |
| 7 | " | 0.28 | 363 | 8.25 | 94.8 | 6.4 | 6.0 | 5.2 | 22.4 | 5.6 | 46.2 | 8.3 |
| 8 | " | 0.61 | 407 | 7.25 | 64.0 | 1.2 | 1.8 | 35.7 | 18.5 | 40.8 | 1.0 | 0.99 |
| 9 | Enelchem[b] TiO$_2$ 2:1 MeOH/ Resorcinol | 0.31 | 385 | 4.00 | 100.0 | 4.8 | 8.8 | — | 12.3 | — | 28.0 | 38.9 |

[a]MeOH = methyl alcohol.
[b]Manufactured by National Lead Company.

fractional distillation vessel may be difficult. The boiling points are: m-methoxy phenol 244.3° C., 2-methylresorcinol 264° C., 4-methylresorcinol 267°–270° C., 5-methylresorcinol 287°–290° C., and resorcinol 275.9° C. and higher methylated resorcinols above 290° C. Preferably, the product mixture is fractionally distilled to obtain a fraction rich in 5-methylresorcinol and a fraction rich in 2-methylresorcinol. Also, a fraction rich in 4-methylresorcinol may be obtained. Each rich fraction is treated in a separate vessel to fractional crystallization from 1,2-dichloroethane with a varied solvent ratio. From this operation the appropriate mono-substituted resorcinol and preferably, predominantly the 5-methylresorcinol along with some 2-methylresorcinol are obtained in a pure state.

After separation, the unreacted resorcinol may be recycled to the reaction vessel directly or indirectly to be mixed with fresh resorcinol and introduced into the reaction vessel. From the separation the products recovered are the desired major amount of 5-methylresorcinol along with a lesser amount of 2-methylresorcinol, and a small amount of 4-methylresorcinol. To further increase the amount of the 5-methylresorcinol produced, after 5-methylresorcinol is separated from the product mixture, the product mixture containing unreacted resorcinol, 2- and 4-methylresorcinol is recycled to the reaction vessel. During the alkylation, these recycled methylresorcinols will undergo, to some degree, isomerization to 5-methylresorcinol.

For a better understanding of the invention reference should be had to the following description and tables from several experimental runs.

The experimental procedure for the runs presented in Table I involved a methanol to resorcinol feed of a 2:1 molar ratio. This feed was pumped over a 30 cm bed (60 ml; 48.4 gm) of Houdry 100S alumina catalyst. The temperature was in the range of 350° to 410° C. and the liquid hourly space velocity (LHSV) was varied within a range of 0.2 to 0.55 volume of reactants per gross volume of catalyst per hour for a total time within the range of 3.0–20 hours. Samples were collected at the bottom of the reaction vessel and analyzed by gas chromatography with the results given in Table I as area percent. It can be seen from Run 8 that the liquid hourly space velocity is a critical parameter. In Run 8 the LHSV was 0.61, which is well out of the range of 0.2 to According to the provisions of the patent statutes, the principle, preferred construction and mode of operation of the invention have been explained and what is considered to represent its best embodiment has been illustrated and described. However, it should be understood that within the scope of the appended claims, the invention may be practiced otherwise than as specifically illustrated and described.

I claim:

1. A process for producing simultaneously the mono-substituted 2-, 4-, and 5-alkylresorcinol isomers, to obtain predominantly the 5-alkylresorcinol isomer along with lesser amounts of the 2- and 4-alkylresorcinol isomer, comprising:

a. reacting an aliphatic alcohol having 1 to 3 carbon atoms selected from the group consisting of; methanol, ethanol, propanol and isopropanol and allyl alcohol and propargyl alcohol and halogenated and nitrated derivates thereof with resorcinol at a molar ratio in the range of greater than 1:1 to 3:1 in the vapor phase at a temperature in the range of about 350° C to around 415° C and in the presence of an acidic catalyst selected from the group consisting of acid activated clays, activated bauxite, alumina, silica-alumina and Friedel-Crafts catalyst under the pressure of at lest atmospheric pressure and for a reaction time until the quantity of 5-alkylresorcinol reaches a maximum whereby a mixture of mono-substituted alkylresorcinol isomers and some other alkylated hydroxy aromatic compounds and some unreacted resorcinol is produced; and b. separating the mono-substituted 2-, 4-, and 5-alkylresorcinol isomers from the other alkylated compounds and unreacted resorcinol in the mixture to obtain predominantly 5-alkylresorcinol and lesser amounts of 2-alkylresorcinol and 4-alkylresorcinol.

2. A process according to claim 1 wherein the reaction is conducted in a continuous operation with a liquid hourly space velocity in the range of about 0.2 to around 0.55 volume of reactants per gross volume of catalyst per hour.

3. A process according to claim 1 wherein the separation is by fractional distillation to obtain distillation fractions rich in one mono-substituted alkylresorcinol and subjecting such distillation fraction to fractional crystallization.

4. A process according to claim 1 wherein the acidic catalyst is composed of 98.5 percent alumina and has a low sodium content.

5. A process according to claim 1 which includes:
recycling 2-alkylresorcinol and 4-alkylresorcinol to the reaction of aliphatic alcohol and resorcinol whereby isomerization occurs to 5-alkylresorcinol.

6. A process for producing simultaneously the mono-substituted 2-, 4-, and 5-methylresorcinol isomers to obtain predominantly 5-methylresorcinol along with lesser amounts of 2-methylresorcinol, and 4-methylresorcinol, comprising:
   a. reacting in the vapor phase at a temperature in the range of about 350° C to around 415° C methanol and resorcinol in a molar ratio in the range of greater than 1:1 to 3:1 in the presence of an acidic catalyst selected from the group consisting of acid activated clays, activated bauxite, alumina, silica-alumina and Friedel-Crafts catalyst and at a pressure of at least atmospheric pressure and at a liquid hourly space velocity in the range of about 0.20 to around 0.55 volume of reactants per gross volume of catalyst per hour whereby a mixture of mono-substituted methylresorcinol isomers and some other methylated hydroxy aromatic compounds selected from the group consisting of m-methoxy phenol and di-, tri-, and tetra-methylresorcinols and some unreacted resorcinol is produced; and
   b. separating the mono-substituted methylresorcinol isomers from the other methylated compounds and unreacted resorcinol in the mixture to obtain predominantly 5-methylresorcinol, along with lesser amounts of 2-methylresorcinol and 4-methylresorcinol.

7. A process according to claim 6 wherein the liquid hourly space velocity is in the range of 0.30 to 0.45 volume of reactants per gross volume of catalyst per hour.

8. A process according to claim 6 wherein the acidic catalyst is composed of 98.5 percent alumina and has a low sodium content.

9. A process according to claim 6 wherein the separation is by fractional distillation to obtain distillation fractions rich in one mono-substituted methylresorcinol and subjecting each distillation fraction to fractional crystallization.

10. A process for producing predominantly 5-methylresorcinol along with a smaller amount of 2-methylresorcinol, comprising:
   a. reacting in the vapor phase methanol and resorcinol in a molar ratio in the range of greater than 1:1 to 3:1 in the presence of a catalyst having 98.57 percent alumina and a low sodium content at a temperature in the range of 350°–385° C. and at a pressure of at least atmospheric pressure and at a liquid hourly space velocity in the range of 0.3–0.45 volume of reactants per gross volume of catalyst per hour whereby a mixture containing 2-methylresorcinol, 4-methylresorcinol, 5-methylresorcinol, m-methoxyphenol, higher methylated resorcinols and unreacted resorcinol is produced;
   b. separating 5-methylresorcinol from the mixture by fractional distillation to produce a 5-methylresorcinol-rich distillation fraction;
   c. recycling the mixture predominantly containing 2-methylresorcinol, 4-methylresorcinol, and unreacted resorcinol to the reaction of resorcinol and methanol whereby isomerization occurs to produce 5-methylresorcinol; and
   d. purifying the 5-methylresorcinol from the 5-methylresorcinol-rich distillation fraction by fractional crystallization.

* * * * *